US010201648B2

(12) United States Patent
Lombardo et al.

(10) Patent No.: US 10,201,648 B2
(45) Date of Patent: Feb. 12, 2019

(54) FILTER MODULE

(71) Applicant: GAMBRO LUNDIA AB, Lund (SE)

(72) Inventors: Eugenio Lombardo, Ponte Nelle Alpi (IT); Stefano Ganzerli, Medolla (IT); Matteo Manfredini, Modena (IT); Marco Morini, Saint Vincent (IT)

(73) Assignee: GAMBRO LUNDIA AB, Lund (SE)

( * ) Notice: Subject to any disclaimer, the term of this patent is extended or adjusted under 35 U.S.C. 154(b) by 7 days.

(21) Appl. No.: 15/327,851

(22) PCT Filed: Aug. 5, 2015

(86) PCT No.: PCT/EP2015/068004
§ 371 (c)(1),
(2) Date: Jan. 20, 2017

(87) PCT Pub. No.: WO2016/020412
PCT Pub. Date: Feb. 11, 2016

(65) Prior Publication Data
US 2017/0209636 A1 Jul. 27, 2017

(30) Foreign Application Priority Data

Aug. 5, 2014 (EP) .................................... 14179850

(51) Int. Cl.
*A61M 1/34* (2006.01)
*B01D 69/02* (2006.01)
(Continued)

(52) U.S. Cl.
CPC ........ *A61M 1/3462* (2013.01); *A61M 1/1672* (2014.02); *A61M 5/165* (2013.01); *B01D 61/28* (2013.01); *B01D 63/087* (2013.01);
*B01D 69/02* (2013.01); *A61M 2005/1655* (2013.01); *A61M 2005/1657* (2013.01); *A61M 2205/75* (2013.01); *B01D 2313/20* (2013.01); *B01D 2313/23* (2013.01); *B01D 2313/58* (2013.01); *B01D 2325/16* (2013.01)

(58) Field of Classification Search
None
See application file for complete search history.

(56) References Cited

U.S. PATENT DOCUMENTS

| 4,276,170 A | 6/1981 | Vaillancourt |
| 4,810,384 A * | 3/1989 | Fabre .................... B01D 71/34 |
| | | 210/500.23 |

(Continued)

FOREIGN PATENT DOCUMENTS

| CN | 101371971 B | * | 4/2012 | |
| EP | 2314332 | | 4/2011 | |
| WO | WO-2011048052 A1 | * | 4/2011 | .......... A61M 1/1656 |

OTHER PUBLICATIONS

CN 101371971 A machine translation—Hong, Yubin et al (Year: 2009).*

(Continued)

*Primary Examiner* — Krishnan S Menon
*Assistant Examiner* — Bradley R Spies
(74) *Attorney, Agent, or Firm* — Barnes & Thornburg LLP

(57) ABSTRACT

The present disclosure relates to a filter module for a medical fluid delivery system capable of removing cytokine inducing substances (CIS) from a medical fluid.

20 Claims, 7 Drawing Sheets

(51) Int. Cl.
  *B01D 63/08* (2006.01)
  *B01D 61/28* (2006.01)
  *A61M 5/165* (2006.01)
  *A61M 1/16* (2006.01)

(56) References Cited

U.S. PATENT DOCUMENTS

| | | | |
|---|---|---|---|
| 2005/0139534 A1* | 6/2005 | Peet | B01D 35/0273 210/167.02 |
| 2007/0131609 A1 | 6/2007 | Ramaswamy et al. | |
| 2011/0163024 A1* | 7/2011 | Zia | A61M 1/0209 210/257.2 |
| 2011/0259810 A1* | 10/2011 | Sakata | B01D 29/111 210/358 |
| 2013/0264266 A1 | 10/2013 | Shick et al. | |

OTHER PUBLICATIONS

15327851_2018-04-10_CN_101371971_A_M—Derwent record for CN 101371971, Hong, Yubin et al (Year: 2009).*
PCT Search Report and Written Opinion for PCT/EP2015/068004, completed Aug. 27, 2015.
Glorieux, Griet, et al., "Looking Beyond Endotoxin: a Comparative Study of Pyrogen Retention by Ultrafilters Used for the Preparation of Sterile Dialyis Fluid," 2014, Scientific Reports. vol. 4, No. 6390, pp. 1-6.

* cited by examiner

FILTER MODULE

CROSS-REFERENCE TO RELATED APPLICATIONS

This application is the U.S. national phase of PCT/EP2015/068004, filed on Aug. 5, 2015, which claims priority to European Patent Application 14179850.4, filed on Aug. 5, 2014. The disclosures of both European Patent Application 14179850.4 and PCT/EP2015/068004 are hereby incorporated herein by reference in their entireties.

TECHNICAL FIELD

The present disclosure relates to a filter module for a medical fluid delivery system capable of removing cytokine inducing substances (CIS) from a medical fluid.

DESCRIPTION OF THE RELATED ART

Medical treatments like hemodialysis, hemodiafiltration and hemofiltration require large amounts of sterile medical fluid. During hemo(dia)filtration, patients are exposed to up to 150 l of substitution fluid, 3 times a week, and 52 weeks a year, which leads to a high volume of fluid directly injected into the patient's blood. It is therefore crucial that the fluid is free of harmful inflammatory substances like bacteria and endotoxins.

It has recently been recognized that not only bacteria and endotoxins, but also cytokine inducing substances (CIS), when present in human blood, can cause clinical consequences such as inflammation status and endothelial damage (e.g. Blood Purif 27 (2009) 81-85; Nephrol Dial Transplant 23 (2008) 3635-3642).

EP 2 314 332 A1 discloses a single use filter module for a medical fluid delivery system. The filter module comprises a positively charged microporous polyethersulfone membrane capable of removing cytokine inducing substances (CIS) from a medical fluid. The incorporation of the filter module into a system for the on-line production of medical fluid leads to an improved medical fluid free from cytokine inducing substances (CIS). FIG. 4 of EP 2 314 332 A1 shows a single use filter module (see FIG. 1) with inlet 18 and outlet 19 positioned on different sides of the housing. Fluid enters the filter module from the upper part 11 and then is filtered through a filter membrane 14 which is a positively charged microporous flat sheet membrane. Any entrapped air passes the deaeration membrane 13 and is purged through the venting slots 12. The bottom part of the housing 15 comprises a support structure 17 to support the membrane and guide the fluid to the outlet 19 and to provide uniform discharge of the fluid.

Hemodiafiltration (HDF) treatments require a wide range of flow conditions, both for extracorporeal blood circulation and for the infusion of sterile saline. Advanced Hemodialysis machines are equipped with two peristaltic pumps for providing the extracorporeal blood purification and for infusing sterile saline during HDF treatments. The combined action of the pumps produces a highly irregular pressure pattern which may include large pressure peaks, so that the filter module for the saline is confronted with large pressure swings during operation.

SUMMARY

It is an object of the present disclosure to further improve the single use module of EP 2 314 332 A1. The present disclosure provides a filter module having improved performance and greatly increased resistance to pressure fluctuations.

DETAILED DESCRIPTION

The housing of the filter module of the present disclosure is made of a polymer material which is biocompatible and suitable for human use. Examples of suitable polymer materials include polyesters; polycarbonates; polyurethanes; acrylonitrile-butadiene-styrene copolymers (ABS); and rigid polyvinylchloride (PVC). For optical control and for visual control, e.g. for air traps, during treatment, the housing preferably is transparent. Examples of suitable polymer materials include polycarbonates (PC); polyethylene terephthalate copolyesters like polyethylene terephthalate glycol-modified (PETG); and polyurethanes (PUR).

Figure 2:
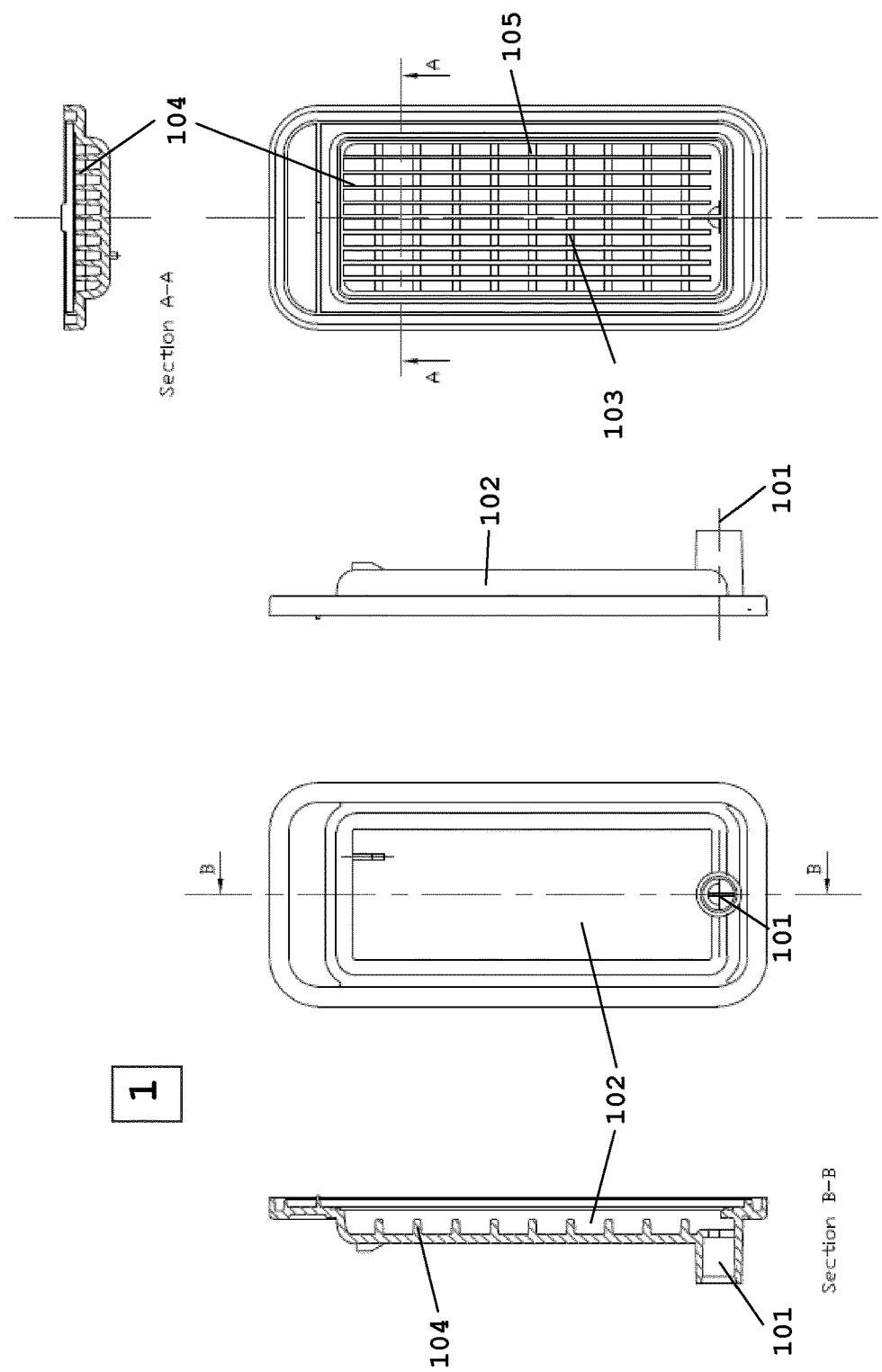
FIG. 2 shows top, bottom, lateral, and two sectional views of the bottom part of an embodiment of the filter module of the present disclosure.
Figure 3:
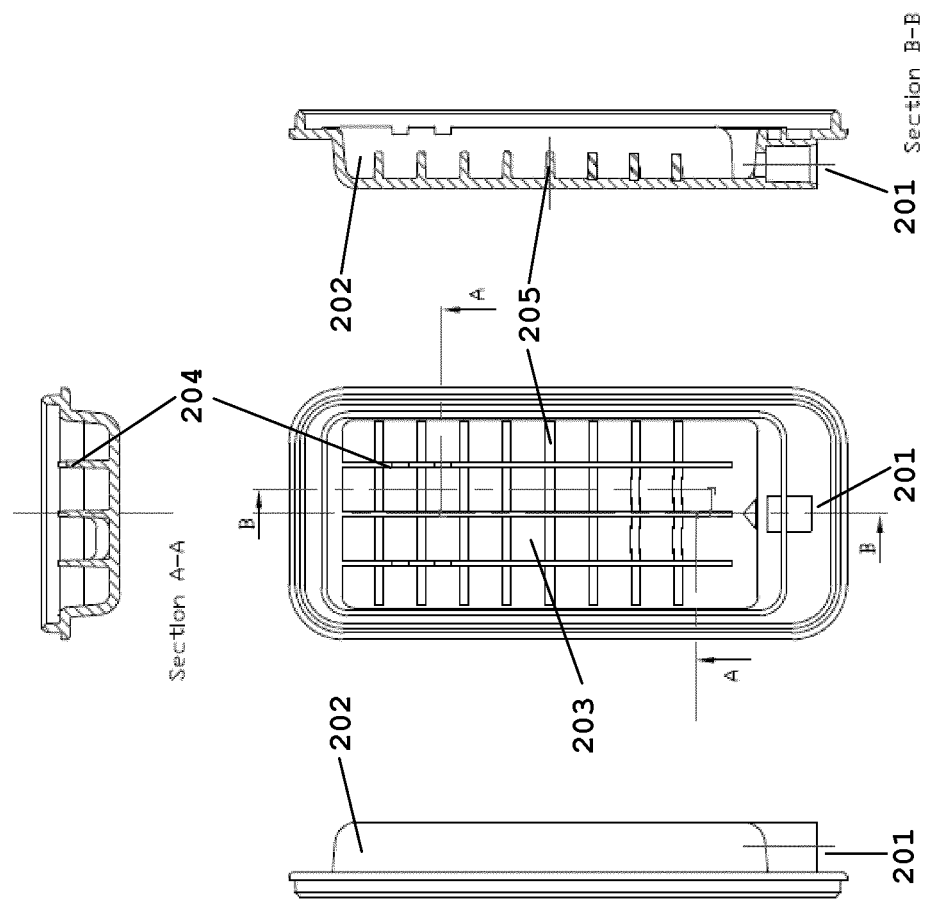
FIG. 3 shows top, bottom, lateral, and two sectional views of the top part of an embodiment of the filter module of the present disclosure.
Figure 3:
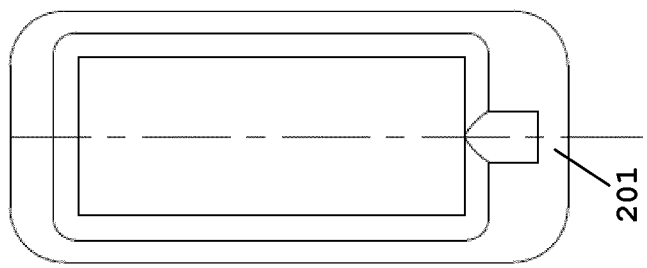

The housing of the filter module is assembled from two components; a bottom part 1 and a top part 2. An embodiment of a bottom part 1 of the filter module of the present disclosure is shown in FIG. 2; an embodiment of a top part 2 of the filter module of the present disclosure is shown in FIG. 3.

The bottom part 1 of the filter module comprises a fluid compartment 102. A fluid outlet 101 is positioned on the center line of the bottom part 1 at one end of the fluid compartment 102.

The fluid compartment 102 contains a support structure 103 consisting of a plurality of longitudinal ribs 104 and transversal ribs 105. The transversal ribs 105 extend from one wall of the fluid compartment 102 to the other wall, reinforcing the fluid compartment 102 and providing additional mechanical stability to the filter module. As a consequence, deformation of the filter module due to pressure variations is minimized. One end of the longitudinal ribs 104 is connected to the wall of the fluid compartment 102 opposite to the end where the fluid outlet 101 is located. The longitudinal ribs 104 do not extend all the way to the other end of the fluid compartment 102, leaving spacing between the end wall of the fluid compartment 102 and the ends of the longitudinal ribs 104. The longitudinal ribs 104 guide the flow of liquid through the fluid compartment 102 and ensure an even flow distribution and smooth discharge of the liquid from the filter module. The spacing is important to merge the flow of the individual channels formed by the longitudinal ribs 104. The longitudinal ribs 104 also support a protection net 301, a positively charged microporous flat sheet membrane 302, and a retention net 303. The height of the longitudinal ribs 104 equals the depth of the fluid compartment 102. The height of the transversal ribs 105 is smaller than the height of the longitudinal ribs 104. In one embodiment, the height of the transversal ribs 105 is in the range of from 40% to 60% the height of the longitudinal ribs 104, for instance, 50% to 60%. The number of longitudinal ribs 104 present in the bottom part 1 of the filter module generally is in the range of from 5 to 11, e.g., 7 to 9. The number of transversal ribs 105 present in the bottom part 1 of the filter module generally is in the range of from 5 to 11, e.g., 7 to 9.

The top part 2 of the filter module comprises a fluid compartment 202. A fluid inlet 201 is positioned on the center line of the top part 2 on one end wall of the fluid compartment 202.

The fluid compartment 202 contains a support structure 203 consisting of a plurality of longitudinal ribs 204 and transversal ribs 205. The transversal ribs 205 extend from one wall of the fluid compartment 202 to the other wall, reinforcing the fluid compartment 202 and providing additional mechanical stability to the filter module. As a consequence, deformation of the filter module due to pressure variations is minimized. One end of the longitudinal ribs 204 is connected to the wall of the fluid compartment 202 opposite to the end where the fluid inlet 201 is located. The longitudinal ribs 204 do not extend all the way to the other end of the fluid compartment 202, leaving spacing between the end wall of the fluid compartment 202 with the fluid inlet 201 and the ends of the longitudinal ribs 204. The longitudinal ribs 204 guide the flow of liquid through the fluid compartment 202 and ensure an even flow distribution within the top part 2 of the filter module. The spacing is important to distribute the inflowing liquid between the individual channels formed by the longitudinal ribs 204. The longitudinal ribs 204 also support a retention net 303, a positively charged microporous flat sheet membrane 302, and a protection net 301. The height of the longitudinal ribs 204 equals the depth of the fluid compartment 202. The height of the transversal ribs 205 is smaller than the height of the longitudinal ribs 204. In one embodiment, the height of the transversal ribs 205 is in the range of from 40% to 60% the height of the longitudinal ribs 204, for instance, 45% to 55%. The number of longitudinal ribs 204 present in the top part 2 of the filter module generally is in the range of from 2 to 6, e.g., 3 to 5. The number of transversal ribs 205 present in the top part 2 of the filter module generally is in the range of from 4 to 10, e.g., 7 to 9.

A protection net 301 is located atop the longitudinal ribs 104 of the bottom part 1. The protection net 301 is a net comprised of a polymer material which is biocompatible and suitable for human use. Examples of suitable polymer materials include polyolefins like polyethylene, polypropylene, or cycloolefin copolymers; polycarbonates; or polyesters like polyethylene terephthalate. In one embodiment, the protection net 301 is a net woven from PET monofilament. The mesh opening of the protection net 301 generally is in the range of from 100 to 600 µm, e.g., from 200 to 300 µm. In one embodiment, the protection net 301 has a mesh opening of 250 to 280 µm. The thickness of the protection net 301 generally is in the range of from 100 to 500 µm, e.g., from 150 to 300 µm. In one embodiment, the protection net 301 has a thickness of 180 to 220 µm. In one embodiment, the weave is not parallel to the edges of the protection net 301, but tilted at an angle in the range of 3 to 30°, e.g., 5 to 10°, for instance, 6° to 9°.

The filter module of the present disclosure comprises a positively charged microporous flat sheet membrane 302. For purposes of the present disclosure, the term "microporous" includes membranes having a pore size of at least 0.1 µm. In one embodiment, the microporous membranes used in the present invention have pore sizes in the range of from about 200 to about 400 nm.

An advantage of the positively charged microporous membrane 302 is that it has excellent retention of cytokine inducing substances (CIS) even if the surface area of the membrane is small, and enables the high fluid flow rates required for the on-line production of medical fluid, e.g., substitution fluid for hemo(dia)filtration. This allows the filter module to be miniaturized and dispenses with the need for a holding tank or reservoir for the medical fluid within the system.

In one embodiment, the microporous flat sheet membrane 302 comprises polyethersulfone. Other options include surface-charged Nylon or cellulose acetate.

The positive charges can be provided by modifying the membrane by adding quaternary ammonium groups to its surface. Modification of the membrane can be achieved by incorporation of a copolymer comprising quaternary ammonium groups into the membrane substrate as shown in U.S. Pat. No. 5,531,893 A, incorporated herein by reference. Modification of the membrane can also be achieved by reacting the membrane substrate with a charge modifying agent like polyethyleneimine epichlorohydrin, as shown in U.S. Pat. No. 5,269,931 A, incorporated herein by reference.

The positively charged microporous membrane 302 is located atop the protection net 301. In one embodiment, the positively charged microporous flat sheet membrane 302 has a thickness of 100 to 180 µm, for instance 120-160 µm, a pore size of about 0.2 µm (e.g. from 0.18 to 0.22 µm), an effective surface area of 8 to 30 cm$^2$, for instance 20 to 30 cm$^2$.

If the surface area is smaller than 8 cm$^2$, retention of cytokine inducing substances (CIS) might be insufficient. If the surface area is larger than 30 cm$^2$, the risk of an uneven flow distribution becomes large and the design of a support structure, which is critical for the membrane, is difficult for high flow rates. The effective membrane surface area has to be selected in order to guarantee a sterility assurance level (SAL) of 6 for the medical fluid.

An example of a positively charged microporous flat sheet membrane 302 suitable for the filter module of the present disclosure is commercially available under the trade name Supor® HP-200 from Pall Corporation.

A retention net 303 is located atop the positively charged microporous membrane 302. The retention net 303 acts as a buffer between the positively charged microporous flat sheet membrane 302 and the longitudinal ribs 204 of the top part 2 of the filter module of the present disclosure. The retention net 303 is comprised of a polymer material which is biocompatible and suitable for human use. Examples of suitable polymer materials include polyolefins like polyethylene, polypropylene, or cycloolefin copolymers; polycarbonates; or polyesters like polyethylene terephthalate. In one embodiment, the retention net 303 is comprised of PET. The thickness of the retention net 303 generally is in the range of from 0.9 to 1.7 mm, e.g., from 1.2 to 1.4 mm. In one embodiment, the weave of the retention net 303 is not parallel to the edges of the retention net 303, but tilted at an angle in the range of 5 to 10°, for instance, 6° to 9°.

In a particular embodiment, the retention net 303 is comprised of three individual layers welded together at their perimeters. The top layer and the bottom layer are nets having a mesh opening in the range of from 400 to 600 µm; e.g., 450 to 550 µm; and a thickness in the range of 250 to 500 µm, e.g., 350 to 450 µm. The intermediate layer is a net having a mesh opening which is larger than that of the top layer and the bottom layer. The mesh opening of the intermediate layer generally is in the range of from 600 to 1000 µm; e.g., 700 to 900 µm. The intermediate layer has a thickness in the range of 400 to 700 µm, e.g., 450 to 550 µm.

The support structure 103, the protection net 301, the retention net 303, and the support structure 203 work together to minimize deformation of the positively charged microporous flat sheet membrane 302 during filtration due to pressure differentials and other causes and effectively prevent rupture of the positively charged microporous flat sheet membrane 302. A further benefit of the protection net 301 is a decrease of transmembrane pressure (TMP) during operation of the filter module, in comparison to an otherwise identical filter module that does not comprise a protection net 301.

In a particular embodiment, the filter module of the present disclosure comprises two positively charged microporous flat sheet membranes 302 separated by an additional protection net 301 instead of a single positively charged microporous flat sheet membrane 302. In this embodiment, the sequence of layers within the filter module thus is, from bottom to top: protection net 301, positively charged microporous flat sheet membrane 302, protection net 301, positively charged microporous flat sheet membrane 302, retention net 303.

Several technologies can be employed to join and seal the parts of the filter module. Examples of useable sealing technologies are heat sealing, heat contact welding, laser welding, ultrasonic welding, RF welding, or friction welding.

In one embodiment, the bottom part 1 and the top part 2 of the filter module are joined by ultrasonic welding.

In one embodiment, the positively charged microporous flat sheet membrane 302 is sealed into the housing of the filter module by heat sealing or heat contact welding. During the sealing process, the polymer material of the housing melts and penetrates into the positively charged microporous flat sheet membrane 302 to provide an additional seal. Due to its pore size, a microporous filter membrane allows for the permeation of the polymer melt, while the pores of an ultrafilter membrane would be too small.

In one embodiment, the protection net 301 and the retention net 303 are sealed into the housing of the filter module by heat sealing or heat contact welding. In another embodiment, the protection net 301 and the retention net 303 are sealed into the housing by ultrasound welding. In still another embodiment, the protection net 301, the positively charged microporous flat sheet membrane 302, and the retention net 303 are welded together by ultrasound or heat welding; and the assembly then is clamped into the housing. In still another embodiment, bonding techniques using materials such as UV bonding materials are employed to affix the membrane 302 and/or the protection net 301 and the retention net 303 to the housing.

Figure 5:
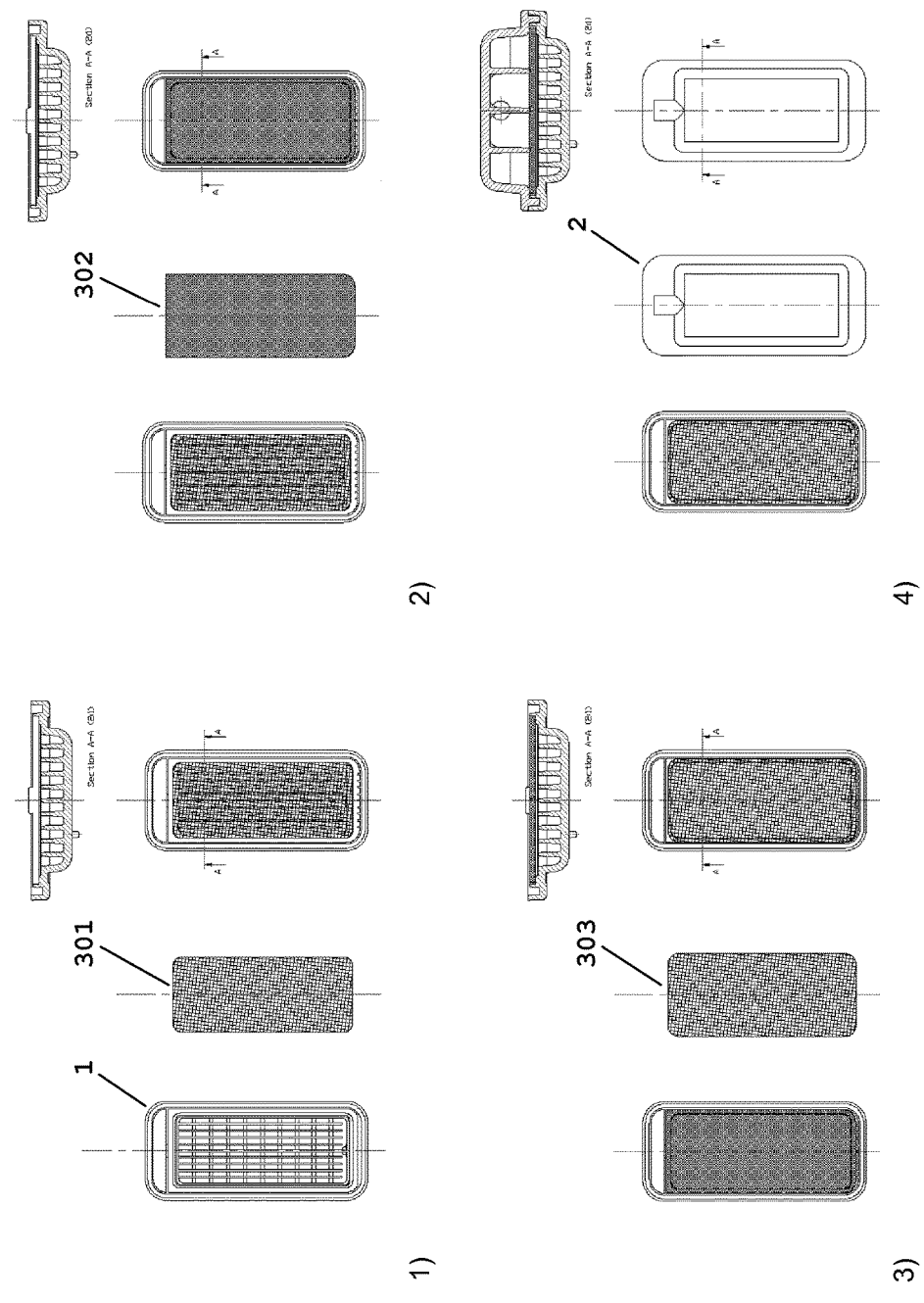
FIG. 5 schematically shows an assembly sequence of an embodiment of the filter module of the present disclosure.

An exemplary assembly sequence of an embodiment of the filter module of the present disclosure is shown in FIG. 5. In step 1, a protection net 301 is positioned in the bottom part 1 of the filter module atop the support structure 103 and affixed to the bottom part 1. In step 2, a positively charged microporous flat sheet membrane 302 is positioned in the bottom part 1 of the filter module atop the protection net 301 and affixed to the bottom part 1. In step 3, a retention net 303 is positioned in the bottom part 1 of the filter module atop the positively charged microporous flat sheet membrane 302 and affixed to the bottom part 1. In step 4, the top part 2 of the filter module is mounted on the bottom part 1; and the top part 2 and the bottom part 1 are bonded to each other to produce a finished filter module of the present description.

An exemplary assembly sequence of another embodiment of the filter module of the present disclosure which comprises two positively charged microporous flat sheet membranes 302 comprises 6 steps. In step 1, a protection net 301 is positioned in the bottom part 1 of the filter module atop the support structure 103 and affixed to the bottom part 1. In step 2, a positively charged microporous flat sheet membrane 302 is positioned in the bottom part 1 of the filter module atop the protection net 301 and affixed to the bottom part 1. In step 3, a second protection net 301 is positioned in the bottom part 1 of the filter module atop the positively charged microporous flat sheet membrane 302 and affixed to the bottom part 1. In step 4, a second positively charged microporous flat sheet membrane 302 is positioned in the bottom part 1 of the filter module atop the second protection net 301 and affixed to the bottom part 1. In step 5, a retention net 303 is positioned in the bottom part 1 of the filter module atop the second positively charged microporous flat sheet membrane 302 and affixed to the bottom part 1. In step 6, the top part 2 of the filter module is mounted on the bottom part 1; and the top part 2 and the bottom part 1 are bonded to each other to produce a finished filter module of the present description.

Examples of medical fluids that can be prepared with a filter module according to the present disclosure are ultrapure dialysis fluid and non-pyrogenic substitution fluid for hemo(dia)filtration. Other examples are peritoneal dialysis fluids, fluids for laparoscopy, biotechnological applications, such as separation of bacteria cultures from solute synthesis products, and similar uses.

Furthermore, such fluids can be used in chip manufacturing or for the exclusion of particles from process water used for chip manufacturing.

The present disclosure also relates to a method for producing a sterile medical fluid free from bacteria, endotoxins and cytokine inducing substances, comprising filtering the medical fluid through a single use filtration module according to the present disclosure.

It will be understood that the features mentioned above and those described hereinafter can be used not only in the combination specified but also in other combinations or on their own, without departing from the scope of the present invention.

The present invention will now be described in more detail in the examples below. It is to be understood that the examples are not intended to limit the scope of the present invention and are merely an illustration of a preferred embodiment of the invention.

EXAMPLES

Example 1

Figure 4:
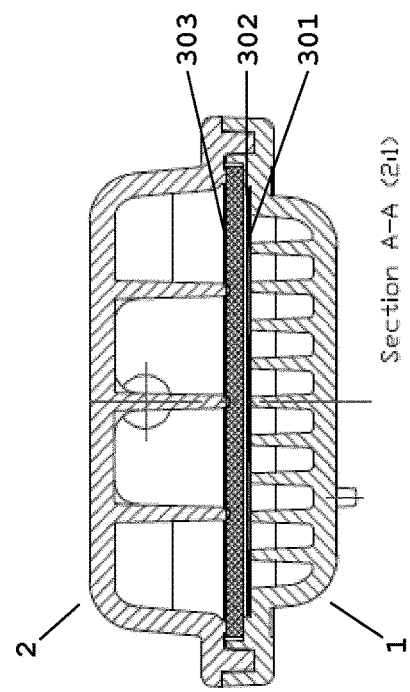
FIG. 4 shows a top view and a sectional view of an embodiment of the filter module of the present disclosure.
Figure 4:
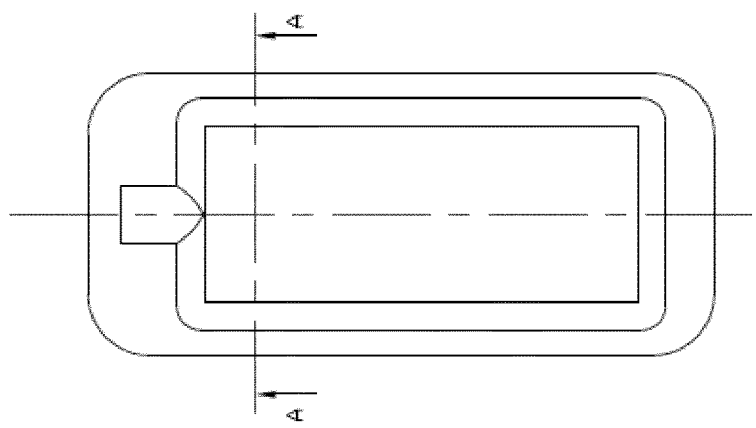
Figure 6:
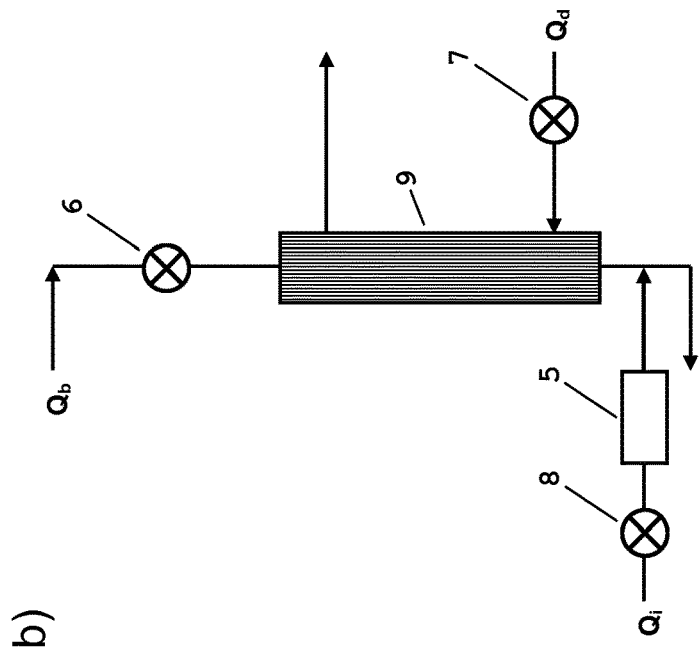
FIG. 6 schematically shows a hemodiafiltration set-up comprising a filter module in the substitution fluid line in a) pre-dilution mode; and b) post-dilution mode.
Figure 6:
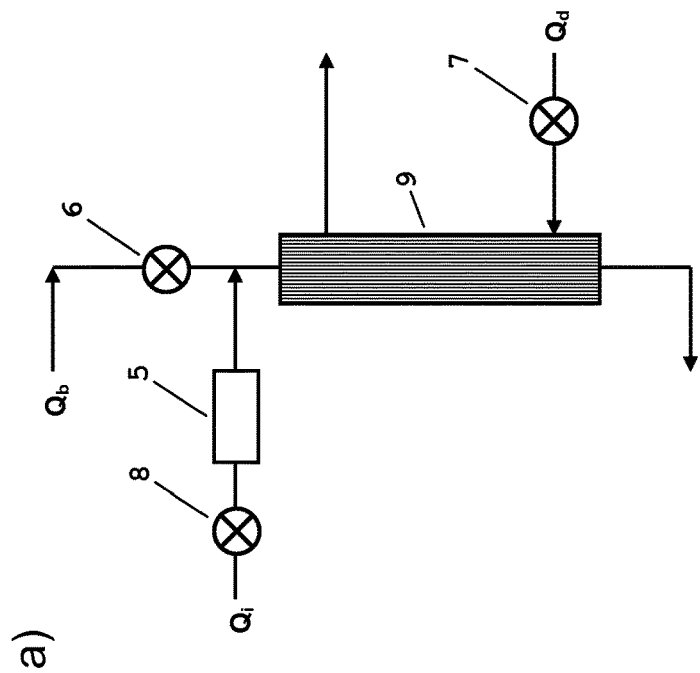

A hemodiafiltration set-up in pre-dilution mode as shown in FIG. 6a was used for the experiment. The set-up comprised a dialyzer 9 (Polyflux® P210H, Gambro Dialysatoren GmbH) mounted on a dialysis machine (AK 200 ULTRA S, Gambro AB) featuring a blood pump 6, a dialysis fluid pump 7, and a substitution fluid pump 8. A filter module 5 as shown in FIG. 4 having an active membrane surface of 25 cm² was provided in the substitution fluid line downstream of the substitution fluid pump 8.

Physiologic saline having a temperature of (37±1)° C. was pumped through the blood side of the dialyzer 9 by pump 6 at a set flow rate of $Q_b$=700 ml/min, and physiologic saline having a temperature of (37±1)° C. was pumped through the filter module 5 by substitution fluid pump 8 and infused into the blood circuit at a position between the blood pump 6 and the dialyzer 9 at a flow rate of $Q_i$=495 ml/min. The pressure post dialyzer was 700 mmHg. After 5 hours runtime, the experiment was stopped. The membrane in the filter module 5 still was intact. The experiment was repeated 4 times, each time using a different filter module 5 of identical build. In each case, the membrane in the filter module 5 was intact after the experiment.

Comparison Example 1

Figure 1:
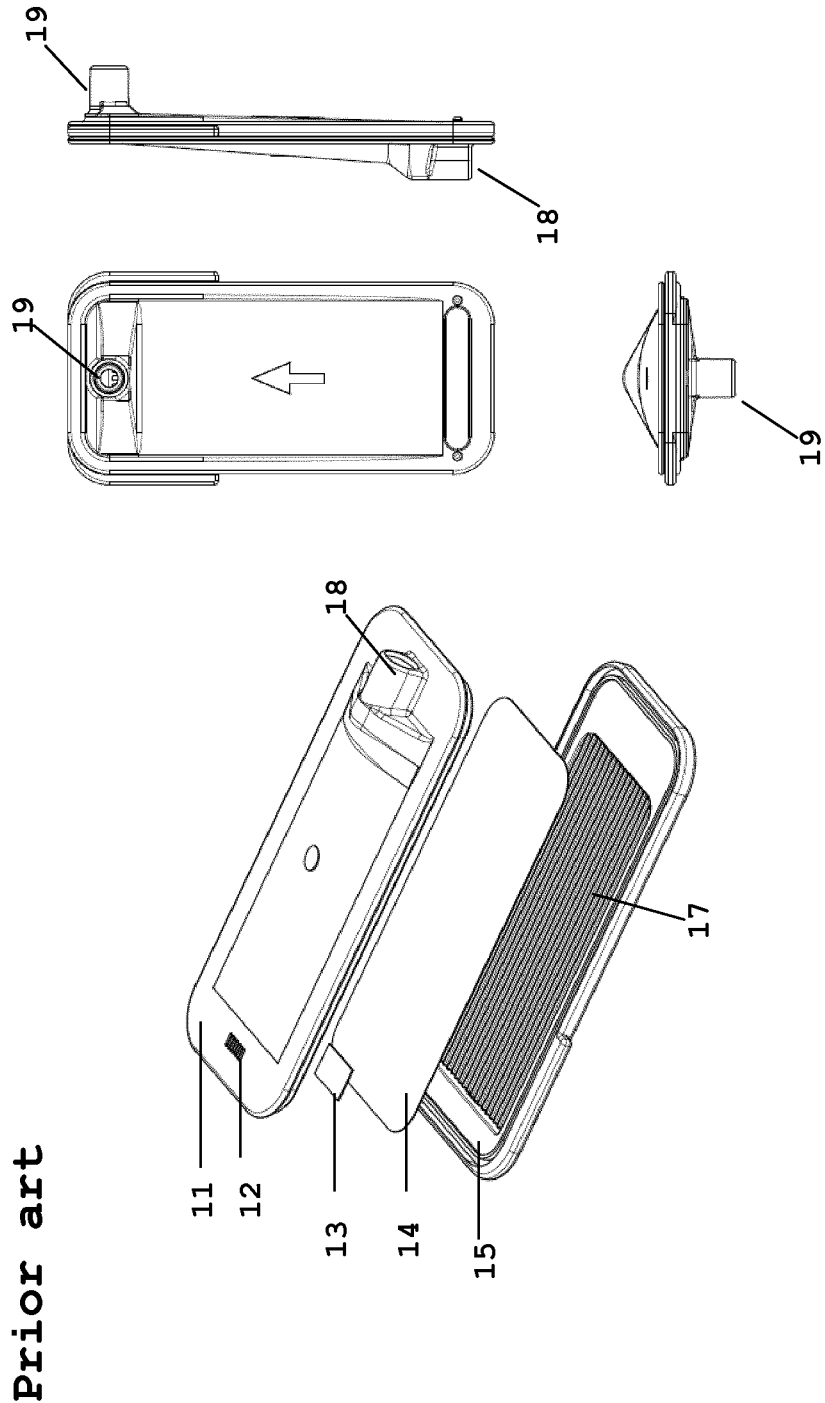
FIG. 1 shows an exploded view, top view, and two lateral views of a prior art single use filter module (FIG. 4 of EP 2 314 332 A1)

Example 1 was repeated using a filter module 5 according to EP 2 314 332 A1 (as shown in FIG. 1) having an active membrane surface of 25 cm² instead of the filter module according to the present disclosure. Rupture of the membrane in the filter module 5 was observed during the experiment. The experiment was repeated 4 times, each time using a different filter module 5 of identical build. In each case, the membrane in the filter module 5 broke during the runtime of the experiment. The time to rupture for the individual runs is listed below.

| Sample # | 1 | 2 | 3 | 4 | 5 |
|---|---|---|---|---|---|
| Time to rupture [min] | 110 | 90 | 95 | 105 | 120 |

Example 2

A hemodiafiltration set-up in post-dilution mode as shown in FIG. 6b was used for the experiment. The set-up comprised a dialyzer 9 (Polyflux® P210H, Gambro Dialysatoren GmbH) mounted on a dialysis machine (AK 200 ULTRA S, Gambro AB) featuring a blood pump 6, a dialysis fluid pump 7, and a substitution fluid pump 8. A filter module 5 as shown in FIG. 4 having an active membrane surface of 25 cm² was provided in the substitution fluid line downstream of the substitution fluid pump 8.

Physiologic saline having a temperature of (37±1)° C. was pumped through the blood side of the dialyzer 9 by pump 6 at a flow rate of $Q_b$=600 ml/min, and physiologic saline having a temperature of (37±1)° C. was pumped through the filter module 5 by substitution fluid pump 8 and infused into the blood circuit at a position downstream of the dialyzer 9 at a flow rate of $Q_i$=50 ml/min. The pressure post dialyzer was 600 mmHg. After 5 hours runtime, the experiment was stopped. The membrane in the filter module 5 still was intact. The experiment was repeated 4 times, each time using a different filter module 5 of identical build. In each case, the membrane in the filter module 5 was intact after the experiment.

Comparison Example 2

Example 2 was repeated using a filter module 5 according to EP 2 314 332 A1 (as shown in FIG. 1) having an active membrane surface of 25 cm² instead of the filter module according to the present disclosure. Rupture of the membrane in the filter module 5 was observed during the experiment. The experiment was repeated 4 times, each time using a different filter module 5 of identical build. In each case, the membrane in the filter module 5 broke during the runtime of the experiment. The time to rupture for the individual runs is listed below.

| Sample # | 1 | 2 | 3 | 4 | 5 |
|---|---|---|---|---|---|
| Time to rupture [min] | 210 | 195 | 170 | 180 | 225 |

Example 3

A filter module 5 as shown in FIG. 4 having an active membrane surface of 25 cm² was connected to the substitution fluid pump 8 of a dialysis machine (AK 200 ULTRA S, Gambro AB). A pressure point measurement was inserted between the substitution fluid pump 8 and the inlet of the filter module 5. Transmembrane pressure (TMP) was determined as the pressure difference (expressed in mmHg) between the filter inlet and the filter outlet, measured at 450 ml/min flow rate. The exit line of the filter was open to air (atmospheric pressure) to obtain a clean TMP read on the pressure point upstream of the filter module 5.

Figure 7:
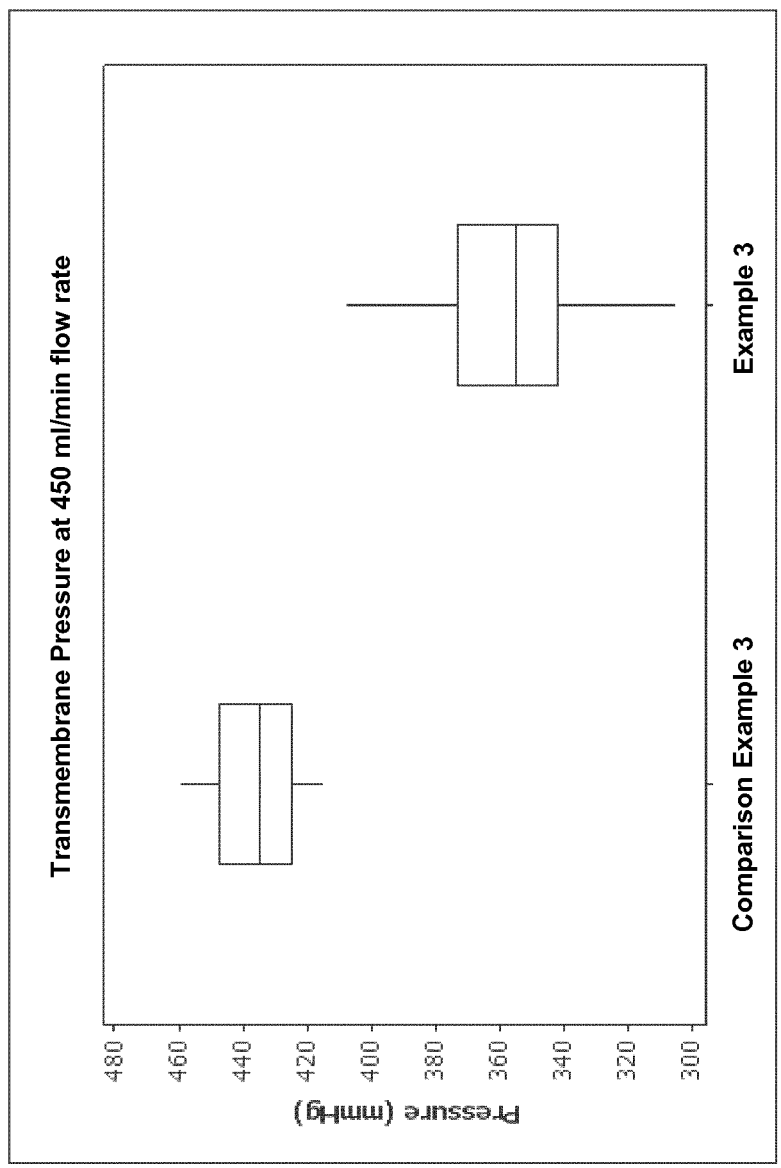
FIG. 7 shows a box plot of the transmembrane pressures (TMP) at 450 ml/min flow rate of a prior art filter module and an embodiment of the filter module of the present disclosure, respectively.

Physiologic saline having a temperature of 40° C. was pumped through the filter module 5 at a flow rate of 450 ml/min. Measurement of TMP was taken after 10 minutes of continuous flow of physiologic saline through the filter module 5. TMP was measured on 40 filter modules 5 of identical build. A box plot of the results is shown in FIG. 7.

Comparison Example 3

Example 3 was repeated using a filter module 5 according to EP 2 314 332 A1 (as shown in FIG. 1) having an active membrane surface of 25 cm² instead of the filter module according to the present disclosure. TMP was measured on 40 filter modules 5 of identical build. A box plot of the results is shown in FIG. 7.

Example 4

A hemodiafiltration set-up in pre-dilution mode as shown in FIG. 6a was used for the experiment. The set-up comprised a dialyzer 9 (Polyflux® P140H, Gambro Dialysatoren GmbH) mounted on a dialysis machine (AK 200 ULTRA S, Gambro AB) featuring a blood pump 6, a dialysis fluid pump 7, and a substitution fluid pump 8. A filter module 5 as shown in FIG. 4 having an active membrane surface of 25 cm² was provided in the substitution fluid line downstream of the substitution fluid pump 8.

Bovine blood (hematocrit 35%) having a temperature of (37±1)° C. was pumped through the blood side of the dialyzer 9 by blood pump 6 at a flow rate of $Q_b$=500 ml/min; dialysis fluid was pumped through the dialysate side of the dialyzer 9 by dialysis fluid pump 7 at a flow rate of $Q_d$=700 ml/min; and physiologic saline having a temperature of (37±1)° C. was pumped through the filter module 5 by substitution fluid pump 8 and infused into the blood circuit at a position between the blood pump 6 and the dialyzer 9 at a flow rate of $Q_i$=195 ml/min. During treatment, the pressure in the arterial line of the dialysis machine was 196±17 mmHg, the pressure in the venous line was −102±14 mmHg. After 6 hours runtime, the experiment was stopped.

Cumulative ultrafiltration volume was 3 l. The membrane in the filter module 5 still was intact.

Example 5

A hemodiafiltration set-up in post-dilution mode as shown in FIG. 6b was used for the experiment. The set-up comprised a dialyzer 9 (Polyflux® P140H, Gambro Dialysatoren GmbH) mounted on a dialysis machine (AK 200 ULTRA S, Gambro AB) featuring a blood pump 6, a dialysis fluid pump 7, and a substitution fluid pump 8. A filter module 5 as shown in FIG. 4 having an active membrane surface of 25 cm² was provided in the substitution fluid line downstream of the substitution fluid pump 8.

Bovine blood (hematocrit 36%) having a temperature of (37±1)° C. was pumped through the blood side of the dialyzer 9 by blood pump 6 at a flow rate of $Q_b$=700 ml/min; dialysis fluid was pumped through the dialysate side of the dialyzer 9 by dialysis fluid pump 7 at a flow rate of $Q_d$=700 ml/min; and physiologic saline having a temperature of (37±1)° C. was pumped through the filter module 5 by substitution fluid pump 8 and infused into the blood circuit at a position downstream of the dialyzer 9 at a flow rate of $Q_i$=100 ml/min. During treatment, the pressure in the arterial line of the dialysis machine was 176±3 mmHg; the pressure in the venous line was −108±3 mmHg. After 6 hours runtime, the experiment was stopped. Cumulative ultrafiltration volume was 3 l. The membrane in the filter module 5 still was intact.

The invention claimed is:

1. A single use filter module capable of on-line production of a medical fluid which is sterile, non-pyrogenic, and free from cytokine-inducing substances, comprising
    a) a housing comprised of
        a1) a bottom part comprising a fluid compartment and a fluid outlet positioned on the center line of the bottom part at one end of the fluid compartment;
        a2) a top part comprising a fluid compartment and a fluid inlet positioned on the center line of the top part on one end wall of the fluid compartment; and
    b) a positively charged microporous flat sheet membrane arranged within the housing, wherein
        i) the bottom part contains a support structure consisting of a plurality of longitudinal ribs and transversal ribs;
        ii) the top part contains a support structure consisting of a plurality of longitudinal ribs and transversal ribs;
        iii) a protection net is arranged within the housing and located atop the longitudinal ribs of the bottom part;
        iv) the positively charged microporous flat sheet membrane is located atop the protection net; and
        v) a retention net is arranged within the housing and located between the positively charged microporous flat sheet membrane and the longitudinal ribs of the top part.

2. The module of claim 1, wherein the height of the longitudinal ribs equals the depth of the fluid compartment; and the height of the transversal ribs is smaller than the height of the longitudinal ribs.

3. The module of claim 1, wherein the protection net is a net woven from PET monofilament.

4. The module of claim 1, wherein the protection net has a mesh opening between about 100 μm to about 600 μm.

5. The module of claim 1, wherein the positively charged microporous membrane comprises polyethersulfone; nylon 6,6; or cellulose acetate.

6. The module of claim 1, wherein the positively charged microporous membrane has a pore size between about 200 nm to about 400 nm.

7. The module of claim 1, wherein the retention net is comprised of PET.

8. The module of claim 7, wherein thickness of the retention net between about 0.9 to about 1.7 mm.

9. The module of claim 7, wherein the retention net is comprised of three individual layers welded together at their perimeters.

10. The module of claim 9, wherein the intermediate layer of the retention net is a net having a mesh opening which is larger than that of the top layer and the bottom layer.

11. The module of claim 10, wherein the intermediate layer of the retention net has a mesh opening between about 600 μm to about 1000 μm; and
    the top layer and the bottom layer having a mesh opening between about 400 μm to about 600 μm.

12. The module of claim 1, comprising two positively charged microporous flat sheet membranes separated by an additional protection net.

13. A method for producing a sterile medical fluid free from bacteria, endotoxins and cytokine inducing substances, comprising filtering the medical fluid through a single use filter module comprising
    a) a housing comprised of
        a1) a bottom part comprising a fluid compartment and a fluid outlet positioned on the center line of the bottom part at one end of the fluid compartment;
        a2) a top part comprising a fluid compartment and a fluid inlet positioned on the center line of the top part on one end wall of the fluid compartment; and
    b) a positively charged microporous flat sheet membrane arranged within the housing, wherein
        i) the bottom part contains a support structure consisting of a plurality of longitudinal ribs and transversal ribs;
        ii) the top part contains a support structure consisting of a plurality of longitudinal ribs and transversal ribs;
        iii) a protection net is arranged within the housing and located atop the longitudinal ribs of the bottom part;
        iv) the positively charged microporous flat sheet membrane is located atop the protection net; and
        v) a retention net is arranged within the housing and located between the positively charged microporous flat sheet membrane and the longitudinal ribs of the top part.

14. The method of claim 13, wherein the sterile medical fluid is non-pyrogenic substitution fluid for hemo(dia)-filtration.

15. A method of removing bacteria, endotoxins, and cytokine inducing substances from fluids, said method comprising the use a single use filter module comprising
    a) a housing comprised of
        a1) a bottom part comprising a fluid compartment containing a support structure consisting of a plurality of longitudinal ribs and transversal ribs; and a fluid outlet positioned on the center line of the bottom part at one end of the fluid compartment;
        a2) a top part comprising a fluid compartment containing a support structure consisting of a plurality of longitudinal ribs and transversal ribs; and a fluid inlet positioned on the center line of the top part on one end wall of the fluid compartment;
    b) a protection net arranged within the housing and located atop the longitudinal ribs of the bottom part;

c) a positively charged microporous flat sheet membrane arranged within the housing and located atop the protection net; and d) a retention net arranged within the housing and located between the positively charged microporous flat sheet membrane and the longitudinal ribs of the top part.

16. The method of claim 15, wherein the height of the longitudinal ribs equals the depth of the fluid compartment; and the height of the transversal ribs is smaller than the height of the longitudinal ribs.

17. The method of claim 15, wherein the protection net is a net woven from PET monofilament.

18. The method of claim 15, wherein the protection net has a mesh opening between about 100 µm to about 600 µm.

19. The method of claim 15, wherein the positively charged microporous membrane comprises polyethersulfone; nylon 6,6; or cellulose acetate.

20. The method of claim 15, wherein the positively charged microporous membrane has a pore size between about 200 nm to about 400 nm.

* * * * *